United States Patent [19]
Haaker et al.

[11] Patent Number: 4,630,296
[45] Date of Patent: Dec. 16, 1986

[54] METHOD OF GENERATING LAYER IMAGES

[75] Inventors: Paul Haaker, Hamburg; Erhard Klotz, Halstenbek; Reiner Koppe, Hamburg; Rolf Linde, Haseldorf; Holger Möller, Hamburg, all of Fed. Rep. of Germany

[73] Assignee: U.S. Philips Corporation, New York, N.Y.

[21] Appl. No.: 755,552

[22] Filed: Jul. 16, 1985

Related U.S. Application Data

[63] Continuation of Ser. No. 537,930, Sep. 30, 1983.

[30] Foreign Application Priority Data

Oct. 9, 1982 [DE]  Fed. Rep. of Germany ....... 3237572

[51] Int. Cl.$^4$ ............................................ G03B 41/16
[52] U.S. Cl. .......................................... 378/2; 378/23
[58] Field of Search .................................. 378/2, 23

[56] References Cited

U.S. PATENT DOCUMENTS

| 3,499,146 | 3/1970 | Richards | 378/23 |
| 4,188,640 | 2/1980 | Dittrich | 378/23 |
| 4,246,483 | 1/1981 | Weiss | 378/23 |
| 4,394,063 | 6/1983 | Weiss et al. | 350/162.13 |

Primary Examiner—Craig E. Church
Attorney, Agent, or Firm—Marc D. Schechter

[57] ABSTRACT

A method of generating layer images from a number of single-shadow images and a device for performing this method. The absorption values associated with the image points of the single-shadow images are stored in a memory. The image value of the layer-image point is formed from the lowest absorption values associated with this layer-image point. Structures or artefacts which are situated outside the layer being imaged can thus be eliminated from the image.

10 Claims, 4 Drawing Figures

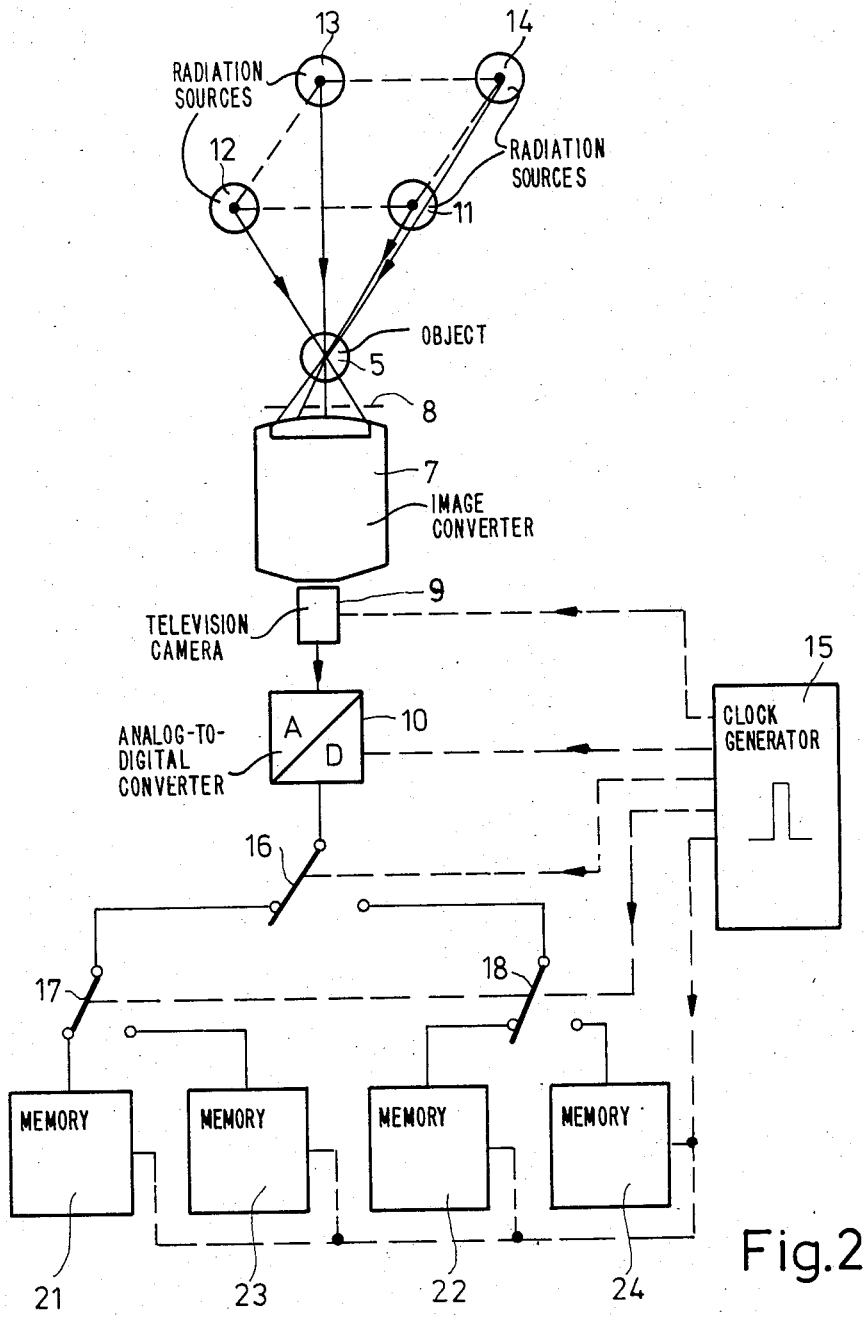

METHOD OF GENERATING LAYER IMAGES

This is a continuation of application Ser. No. 537,930, filed Sept. 30, 1983.

BACKGROUND OF THE INVENTION

The invention relates to a method of generating images of layers of an object. The object is irradiated from a plurality of radiation source positions in order to generate separate single-shadow images. For each single-shadow image, measurement values are recorded, depending on the absorption at each image point. For each layer image, an image value is recorded for each layer-image point. The image value at each image point is derived from the recorded measurement values of the image points of the single-shadow images which are geometrically associated with the layer-image point.

An image point (or shadow-image point) is to be understood to mean herein a single-shadow image zone which has finite dimensions and which is preferably square. A layer-image point is to be understood to mean a corresponding zone in the layer image.

A method of this kind is described in U.S. Pat. No. 3,499,146. In this method the single-shadow images are generated by an X-ray source which is successively moved to different positions. The radiation pattern is recorded by an image converter, for example an image intensifier whose exit screen image is scanned by a television camera.

The video signal generated by the television camera represents the successive measurement values associated with the individual image points of the single-shadow image. The video signal can be stored in a digital or analog storage device.

The image value associated with a layer image point is derived from the shadow-image points which are geometrically associated with the layer-image point (i.e. those images points which are situated on the connecting line between the relevant layer-image point and the various radiation source positions during the exposure) by adding these measurement values. Additional steps may be taken to exclude values which deviate substantially from the other measurement values.

Due to the described superposition of the measurement values associated with the corresponding shadow-image points of the single-shadow images, details which are situated outside the imaged layer do not appear as strongly in the image of a layer image point than if they were situated in this imaged layer. Such points are thus "blurred" as in other tomography methods.

For objects which have comparatively spatially uniform absorption, suitable results are obtained by this method. However, for imaging objects having very inhomogeneous spatial absorption, for example coronary arteries filled with a contrast medium, the highly absorbent details situated outside the imaged layer are imaged several times in the layer. Such details appear more intense as the number of radiation source positions is decreased or the number of single-shadow images is decreased. These artifacts substantially influence the evaluation of such layer images.

SUMMARY OF THE INVENTION

It is an object of the present invention to provide a method of producing useful images of layers of objects with only a few single-shadow images.

This object is achieved, according to the present invention, by forming the image value from the measurement value which corresponds to the lowest absorption.

The invention is based on the following idea. If an object were to consist of only one thin layer, the absorption or the intensity would be the same in all image points of the single-shadow images associated with a given layer-image point. The absorption would depend only on the absorption in the layer-image point. In real objects, however, absorbing structures are usually present on both sides of the layer. Consequently, the intensities of the image points in real objects are lower than in the hypothetical case, and these intensities usually differ from one another. The deviations of the intensities increase as absorption due to structures outside the image layer increases. In other words, the highest intensity value has been least influenced by absorbing structures outside the imaged layer, so that it is the best measure of the absorption in the layer-image point.

Consequently, if only the highest intensity value is used as a basis for the image value for each layer-image point, the artifacts in the image of this layer (which are caused by absorbing structures outside the layer) are substantially suppressed. The method according to the invention thereby forms useful layer images from only four single-shadow images (radiation source positions).

In a further version of the method according to the invention, the image value associated with a layer-image point is subsequently subtracted from the measurement values of the single-shadow-image points geometrically associated with this layer-image point. The new measurement values thus calculated are then used for generating images of other layers in the object.

This variation is based on the following idea. When the measurement value which corresponds to the highest intensity or the lowest absorption is determined solely by the absorption in the layer-image point, a corresponding component must also be present in the measurement values of the other shadow-image points geometrically associated with the layer-image point. This component is eliminated from each shadow-image point by the subtraction operation (assuming that the measurement values correspond to the logarithm of the radiation intensity in the relevant shadow-image points). Consequently, when generating images of other layers of the object, this component can no longer influence the image values of the layer-image points of the other layer. As a result, the accuracy is enhanced.

A device for performing this method comprises a radiation source array for generating a plurality of single-shadow images of the object. Each single-shadow image is generated from one radiation source position. The device also includes an image converter unit for converting each single-shadow image into electrical signals. A storage device is provided for storing the signals associated with the image points of the single-shadow images, and means are provided for retrieving the signals associated with the image points which are geometrically associated with a layer-image point. A value derived from these image points is applied to an image display unit.

According to the invention, the signals retrieved from the storage device are applied to an extreme-value decoder. The output of the signal of the decoder forms the signal which corresponds to the lowest absorption.

In a further version of this device, the storage device comprises a number of storage sections. Each storage section corresponds to a radiation source positions and stores the signal values associated with the image points of a single-shadow image. The storage sections are simultaneously and independently addressable.

An image of the layer is displayed point-by-point so that it is synchronized with the storage sections. Each layer-image point is displayed as its geometrically associated image points are retrieved from the storage sections. This provides real-time processing (i.e. the image values of the layer-image points are formed as quickly as they are displayed by the display unit, for example a television monitor).

BRIEF DESCRIPTION OF THE DRAWING

FIG. 2 schematically shows a device for generating single-shadow images and for storing the measurement values associated with the image points of the single-shadow images.

DESCRIPTION OF THE PREFERRED EMBODIMENTS

Figure 1:
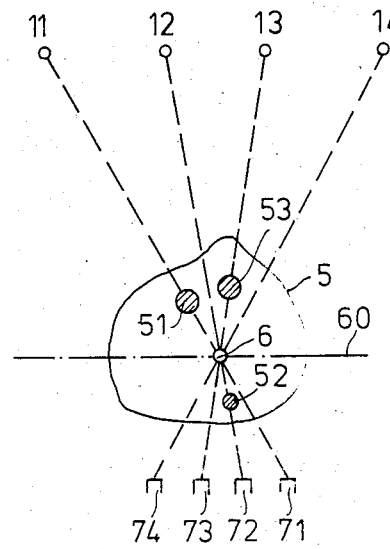
FIG. 1 schematically illustrates the principle of the invention.

FIG. 1 shows an object 5 which is irradiated from a plurality of radiation source positions by a single movable radiation source or by a plurality of radiation sources 11, 12, 13 and 14. Each source limits radiation of the same intensity. Each source irradiates the volume element 6 in a layer 60 in the object.

The intensity of the radiation passing through the layer-image point 6 is measured by the converters 71, 72, 73 and 74 arranged behind the object 5. The radiation absorbing structures, for example arteries filled with a contrast medium, are concentrated at some locations in the object, inter alia at the areas 51, 52 and 53 which are situated within the beams of the radiation sources 11, 12 and 13 which pass through the layer image point 6. Consequently, the converters 71, 72 and 73 associated with these radiation sources measure a substantially lower intensity (or a higher absorption) than the converter 74. This is because the intensity of the radiation from the source 14, which is measured by converter 74, is hardly influenced by highly absorbing structures which are situated outside the layer 60.

If the image value associated with the layer-image point 6 were to be generated by superposition of the measurement values generated by the converters 71–74, as in the conventional methods, the image value obtained would correspond to a high absorption at the layer-image point 6, even when the actual absorption at this point was only very low. In other words, the structures 51, 52 and 53 which are situated outside the layer would be projected into the image of the layer.

Figure 4:
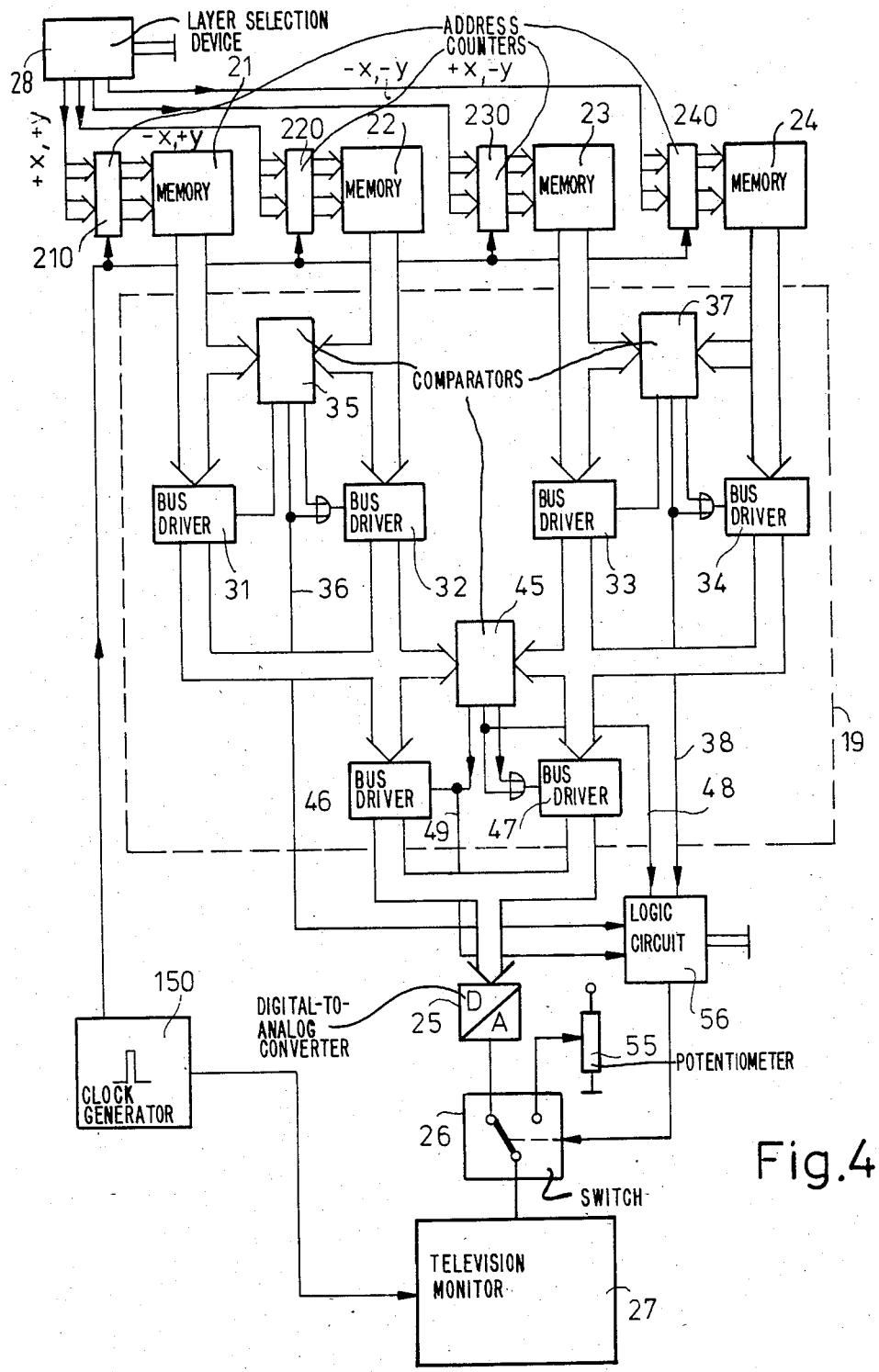
FIG. 4 schematically shows a device for determining an displaying the image values of the layer-image points.

These artifacts are avoided, however, when only the measurement value which is produced by the converter 74, and which corresponds to the lowest absorption or the highest intensity, is output as the image value of the layer-image point 6. The structures 51, 52 and 53 situated outside the layer then do not affect the image value of the layer image point 6 (i.e. they are not imaged in the layer). The device shown in FIGS. 2 and 4 is based on this method.

The device shown in FIG. 2 comprises the four radiation sources 11–14 (preferably X-ray sources) which are arranged so that their focal points are situated at the corners of a square. During operation the four radiation sources can emit radiation beams which are represented by straight lines in the drawing. However, the radiation beams actually cover the entire object 5 and substantially intersect in a plane which is parallel to the plane of the square and which preferably also intersects the object 5. The radiation sources emit radiation of the same intensity for the same period of time.

It follows from the description given with reference to FIG. 1 that it is an essential aspect of the invention that the single-shadow images are separated (i.e. the image points of a single-shadow image may be generated only by one of the four sources). This could in principle be achieved by successively activating the sources or by moving a single source successively to the different positions. Each single-shadow image is then stored before the next single-shadow image is formed. The object 5 would then be irradiated at different instants, which could cause a lack of focus in the case of moving or moved objects.

Alternatively, the converter unit for converting the spatial radiation intensity pattern into electrical measurement values could be arranged at such a distance from the object 5 that the radiation patterns produced by the four sources would be situated adjacently on the entrance surface of the converter unit. However, in that case it would be necessary to increase the radiation dose and to increase the entrance surface.

In order to generate separate single images, a two-dimensional grid 8, as described in German Pat. No. 2,546,785, is used. This grid is arranged in a plane parallel to the plane of the square and comprises as many square apertures as there are image points required in the single image (for example 256×256 or 512×512). The grid 8 is arranged between the object 5 and a converter unit 7 so that four image points are irradiated through each aperture by the four sources 11–14. The four image points are situated adjacent other image points (without overlapping) which are irradiated through neighbouring apertures.

Figure 3:
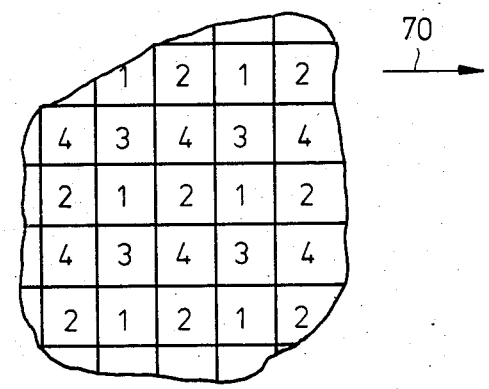
FIG. 3 schematically shows a portion of the radiation pattern generated by the device shown in FIG. 2.

Consequently, an image is formed on the entrance surface of the image converter unit 7. A portion of the image is shown in FIG. 3. The reference numerals 1, 2, 3, and 4 denote image points produced by the sources 11, 12, 13, and 14, respectively, via the various apertures in the grid 8. As appears from FIG. 3, the image points on every second line are alternately generated by the sources 11 and 12, while the image points on the intermediate lines are generated by the sources 13 and 14.

The image converter unit can in principle be a matrix of semiconductor detectors whose dimensions correspond to the dimensions of the image points. The number of detectors is four times larger than the number of image points in a single-shadow image, so that each of the image points produced by the four radiation sources can be detected by a separate detector.

However, such a detector array is comparatively complex. Consequently, an image intensifer 7 is used instead. The intensity pattern on the entrance screen of image intensifier 7 corresponds to the separate single-shadow images, interleaved according to FIG. 3. The intensity pattern appears on the exit screen of the image intensifier at a reduced scale but with a substantially higher intensity to form an exit image.

The exit image is recorded by a television camera 9. When the television camera 9 scans lines of the image on the exit screen in the direction of the arrow 70 in FIG. 3, and when the number of lines of the television camera is twice the number of image point lines in a single image (512 lines for 256×256 image points per single image or 1024 lines for 512×512 image points per single image), one row of image points (shown in the detail of FIG. 3) is scanned per line.

For each line, the video signal produced by the television camera is scanned twice as often as there are image points in the rows of a single image (i.e. for the given examples 512 times or 1024 times, respectively). The video signal is converted into a binary number or digital data word by an analog-to-digital converter 10. The number or word is a measure of the intensity or absorption corresponding to the relevant image point.

Prior to digitizing, preferably the logarithm of the video signal is computed or its dynamic range is reduced by an appropriate compandor. During this operation, it must be ensured that the binary numbers remain reversibly unambiguously associated with the absorption or the radiation intensity corresponding the single image points.

The device further comprises four digital memories 21, 22, 23, and 24, each of which is associated with one of the sources 11, 12, 13, and 14 (i.e. each of these memories stores the data words associated with the image points generated by the associated source 11-14). To this end, the output line of the analog-to-digital converter (in reality a data bus) is connected, via a first demultiplexer 16 which is shown as a switch, to the inputs of two further demultiplexers 17 and 18. The outputs of the demultiplexer 17 are connected to the data inputs of the memories 21 and 23, while the outputs of the demultiplexer 18 are connected to the data inputs of the memories 22 and 24.

A clock generator 15 (i) generates the synchronization signals for the television camera 9, (ii) switches the demultiplexer 16, and (iii) sets the length of the data words generated by the analog-to-digital converter. Consequently, the data words generated by the analog-to-digital converter 10 are applied alternately to the memory 21 and to the memory 22 via the demultiplexer 16 for as long as the demultiplexers 17 and 18 remain in the positions shown in the drawing. When the data words thus generated correspond to the absorptions or intensities in the image point row 1, 2, 1, 2 ... (see FIG. 3), the data words associated with the image points 1 (FIG. 3) are transferred to the memory 21. The data words associated with the image points 2 are transferred to the memory 22. The addressing of these memories is controlled by the clock generator 15 at half the clock frequency of the analog-to-digital converter 10.

At (or directly before) the beginning of the next television line, the demultiplexers 17 and 18 are switched to the positions which are not shown in FIG. 2. As a result, the data words associated with the image points 3 and 4 in FIG. 3 are written in the memories 23 and 24. During the next line, the demultiplexers 17 and 18 are again returned to the position shown in FIG. 2, and so on. When the television camera 9 has converted the complete exit screen image of the image intensifier 7 into a video signal, the intensity or absorption distributions of the single images generated by the four X-ray sources 11-14 have been stored in each of the memories 21-24.

In order to generate an image of the layer in which the radiation beams emitted by the four X-ray sources 11-14 register, the first data word stored in each of the memories 21, 22, 23 and 24 is read and applied to the four inputs of an extreme-value decoder 19 via corresponding bus lines. The largest data word on the four inputs of decoder 19 (corresponding to the highest intensity) is conducted by the decoder to its single output.

A digital-to-analog converter 25 is connected to the output of decoder 19. Converter 25 is connected to a television monitor 27 via a switching device 26.

Subsequently, the next four data words are simultaneously read from the memories 21-24. The clock generator 150 applies clock pulses to the address counters 210, 220, 230 and 240 associated with the memories 21, 22, 23 and 24. It also applies clock pulses to the deflection generators of the television monitor 27, so that the counters and monitor are synchronized in such a manner that the data words which have been converted into analog signals appear on the video input of the television monitor 27 at the rate required to form a television image of the layer.

When images of other layers are to be generated, it is necessary to retrieve the data words which are associated with the image points geometrically associated with the relevant layer image point to be generated. These data words are not stored at the same address in the memories 21-24. Consequently, the addresses must be modified for each layer to be imaged.

When single images comprising, for example, 256×256 image points are to be processed, modification of the addresses to produce images of different layers is comparatively simple when the position of an image point within an image point row or line is determined by the last eight binary positions of the address and the position of an image point row within a single image is determined by the first eight binary positions of the address word. The last eight binary positions of the addresses for the memories 21 and 24 (which are associated with the sources 11 and 14 and whose connecting line extends perpendicular to the direction of the image point row) must then be modified by the same amount (for example +x). The last eight binary positions of the addresses for the memories 22 and 23 must be modified by the same amount as the addresses for memories 21 and 24, but these modifications must be in the opposite direction.

The first eight binary positions of the addresses for the memories 21 and 22 must be modified by the same amount (e.g. +y). The first eight binary positions of the addresses for memories 23 and 24 must be modified the same amount, but with the opposite sign (−y).

The required address offset can be readily achieved by using presettable binary counters, whose values (x, y) can be preset in the described manner, for the address counters. This can be performed, for example, by means of a layer selection device 28 which is operated by the operator, for example by way of a keyboard or an analog input device. Thus, at a later stage the single images can be used to form images of arbitrary layers whose position is unambiguously determined by the parameters x and y.

The extreme-value decoder 19 will now be described in detail. It comprises four bus drivers 31, 32, 33 and 34 whose inputs are connected to the data outputs of the associated memories 21, 22, 23 and 24, respectively, via a bus line. The input signal of each a bus driver 31-34 appears (after amplification) on its output when an appropriate signal is present on its enable input.

The enable inputs of the bus drives 31 and 32 are controlled by a comparator 35 whose inputs are connected to the outputs of the memories 21 and 22 via bus lines. The comparator 35 comprises two outputs which indicate whether the binary number present on the output of the memory 21 or that on the output of the memory 22 is larger. A third output 36 can indicate that both binary numbers are equal. The three outputs of the comparator 35 are connected, directly or via an OR-junction, to the enable inputs of the bus drivers 31 and 32 so that the bus driver 31 is enabled when the binary number supplied by the memory 21 is larger than the binary number on the output of the memory 22. The bus driver 32 is enabled when the binary number on the output of the memory 22 is equal to or larger than the binary number on the output of the memory 21. Consequently, the larger one of the two binary numbers is always present on the common output of the bus drivers 31 and 32.

Similarly, the bus drivers 33 and 34 are controlled by a comparator 37 so that the larger one of the two binary numbers is always present at their common output. The output 38 of the comparator 37 can also indicate that both binary numbers are equal.

The output of the bus drivers 31 and 32 on the one hand, and the output of the bus drivers 33 and 34 on the other hand are connected to the inputs of a third comparator 45 as well to further bus line drivers 46 and 47 respectively. The drivers 46 and 47 are controlled by the comparator 45 so that their common output, which is connected to the input of the digital-to-analog converter 25, bears the larger one of the two binary numbers or, should both binary numbers be equal, either one of these binary numbers. The digital-to-analog converter 25 thus always receives the largest one of the binary numbers present on the outputs of the four memories 21-24. Should more than one binary number be maximum, any one of these binary numbers is present at the output of decoder 19.

Alternatively, the extreme-value decoder 19 should always produce the smallest binary number on its output when the video signal is stored in the memories 21-24 in such a form that the lowest absorption or the highest intensity is associated with the smallest binary numbers. In that case, the enable inputs of the two bus drivers (for example drivers 31 and 32) controlled by a single comparator must be interchanged.

When the measured intensities of three of the four image points associated with a layer image point (for example layer-image point 6 in FIG. 1) are substantially lower than the intensity of the fourth image point, the cause may be (a) that three radiation sources irradiate, in addition to the layer-image point 6, further absorbing structures (such as 51-53 in FIG. 1) which are situated outside the layer, or (b) that a measurement error is involved. This means that when only one maximum value is found, there is always uncertainty as to whether this measurement value is actually determined by the absorption conditions in the layer-image point, or whether it is determined by a measurement error. However, when there are at least two substantially equal maximum values, a measurement error is less likely to be involved. This is even more so when there are three or even four substantially equal maximum values. This means that the layer image is composed of image values for which the probability of correct measurement may fluctuate from one layer-image point to another.

Layer-image points associated with only one or two maximum values (and which are therefore less reliable than layer-image points associated with more maximum values) can be suppressed by connecting the video input of the television monitor 27 to a suitable voltage (to be derived, for example, from a potentiometer 55), instead of to the output of the digital-to-analog converter, whenever there are less than a selected number of maximum values. This connection can be made by a switch 26.

The switch 26 is controlled by a logic circuit 56. Circuit 56 combines the signals on the lines 36, 38 and 48 of the comparators 35, 37 and 45, respectively, and one of the two other output lines of the comparator 45. The signals on these four lines unambiguously indicate whether there are one, two, three or four maximum values. Preferably, the logic circuit 56 is constructed so that the operator can preset, using a suitable input device, how many of the four binary numbers supplied by the memories must correspond to the maximum value.

As already explained, the binary numbers need not be exactly equal, but should at least approximate the maximum value. Consequently, the comparators 35, 37 and 45 need not receive all binary positions of the binary numbers. They need only the most significant binary positions.

The operator can thus preset the degree of reliability for the individual layer image points.

It follows from the above description that from the four single-shadow images recorded by simultaneously activating the X-ray sources 11-14, images can be formed of preselected layers and with preselected probabilities that the layer-image points are not based on measurement errors. The period of time required for forming such a layer image corresponds to the duration of two television images and the switch-on period.

Alternatively, the four X-ray sources can be periodically activated in order to record dynamic processes and in order to form layer images therefrom by tomoscopy. Furthermore, when the television signals corresponding to the series of images thus generated are stored in a suitable memory (for example on magnetic tape), postprocessing is possible.

It is alternatively possible to process single-shadow images which are successively generated by, for example, two adjacent X-ray sources. They can be processed as images of a stereo video film. Each single-shadow image can be reproduced as a video film. Alternatively, each image can also be displayed as a stationary image.

The method according to the invention is particularly suitable for generating images for digital subtraction angiography. In order to perform the subtraction in the time or energy mode, the hardware described with reference to FIG. 4 can be used. For recording in the energy mode, the tubes should be successively operated with different voltages.

It is also feasible to use film or Fuji plates in the method according to the invention. It is particularly advantageous to use a planar image carrier in order to avoid image geometry errors.

The film images can be digitized by means of known film scanners (e.g. Optronix-Photoscan). However, a lens matrix (lenses arranged at positions corresponding to the positions of the X-ray tubes), which successively projects the various perspective images (via shutters) onto a television camera, may alternatively be used.

Further processing is then performed according to FIG. 2. (A lens matrix for decoding layers is described in U.S. Pat. No. 4,394,063.)

Before being processed to form layer images, the single-shadow images can in principle be preprocessed by known methods (for example high-pass filtering, differentiation, etc.).

In addition to the four recording tubes, a fifth tube may be arranged in the center of the tubes for the positioning the patient and for catheterization of vessels.

What is claimed is:

1. A method of generating an image of a layer of an object, said image being made up of a plurality of layer-image points, said method comprising the steps of:
    irradiating the object from a plurality of radiation source positions to generate separate single-shadow images of the object, each single-shadow image being made up of a plurality of shadow-image points, each shadow-image point having an image value representing an amount of radiation absorbed by the object; and
    generating the layer-image points from the single-shadow images to form the image of the layer;
    characterized in that an image value of each layer-image point is generated by:
    selecting one shadow-image point from each shadow image, each selected shadow-image point being geometrically associated with the layer-image point, said shadow-image points forming a set of shadow-image points associated with the layer-image point;
    comparing the image values of the shadow-image points in the set of shadow-image points to determine the image value corresponding to the lowest amount of radiation absorbed by the object; and
    assigning an image value to the layer-image point, the image value being proportional to the image value of the shadow-image point corresponding to the lowest amount of radiation absorbed by the object.

2. A method as claimed in claim 1, characterized in that images of other layers of the object are generated from the single-shadow images by first subtracting, from each shadow-image point in the set of shadow-image points associated with the layer-image point, the image value of the shadow-image point in the set corresponding to the lowest amount of radiation absorbed by the object.

3. A method as claimed in claim 1, characterized in that the method further includes the step of determining the number of shadow-image points, in the set of shadow-image points associated with the single layer-image point, having image values approximately equal to the image value of the shadow-image point in the set corresponding to the lowest amount of radiation absorbed by the object, in order to estimate the likelihood of measurement errors.

4. A device for generating an image of a layer of an object, said image being made up of a plurality of layer-image points, said device comprising:
    means for irradiating the object from a plurality of radiation source positions to generate separate single-shadow images of the object, each single-shadow image being made up of a plurality of shadow-image points, each shadow-image point having an image value representing an amount of radiation absorbed by the object;
    an image converter unit for converting the image value of each shadow-image point into an electrical signal;
    a storage device for storing the electrical signals corresponding to the shadow-image points;
    means for retrieving the electrical signals corresponding to shadow-image points geometrically associated with each layer-image point whose image value is to be generated, said electrical signals forming sets of signals associated with each layer-image point whose image value is to be generated;
    an extreme-value decoder for comparing the electrical signals in each set of signals associated with each layer-image point to determine the electrical signals corresponding to the lowest amounts of radiation absorbed by the object; and
    means for constructing an image of the layer from the electrical signals corresponding to the lowest amounts of radiation absorbed by the object at each layer-image point.

5. A device as claimed in claim 4, characterized in that:
    the storage means comprises storage sections for separately storing the electrical signals for each single-shadow image, said storage sections being simultaneously and independently addressable; and
    the device further comprises a display unit synchronized with the storage sections for displaying each layer-image point immediately after its associated electrical signals are retrieved from the storage sections.

6. A device as claimed in claim 4, characterized in that the irradiation means comprises an X-ray source arranged at each radiation source position.

7. A device as claimed in claim 6, characterized in that the device further comprises a grid arranged between the X-ray sources and the image converter unit, said grid having a number of apertures equal to the number of image points in a single-shadow image, each image point on the image converter being irradiated by one X-ray source only.

8. A device as claimed in claim 7, characterized in that there are four X-ray sources, one located at each corner of a square.

9. A device as claimed in claim 8, characterized in that the extreme-value decoder comprises:
    first and second gate circuits having a common output, each gate circuit having an input coupled to an output of a storage section;
    a first comparator for comparing the outputs of the storage sections coupled to the first and second gate circuits and for enabling either the first or second gate circuit but not both;
    third and fourth gate circuits having a common output, each gate circuit having an input coupled to an output of a storage section;
    a second comparator for comparing the outputs of the storage sections coupled to the third and fourth gate circuits and for enabling either the third or fourth gate circuit but not both;
    fifth and sixth gate circuits having a common output which is the output of the extreme-value decoder, each gate circuit having an input coupled to a common output of the first and second or third and fourth gates; and
    a third comparator for comparing the common output of the first and second gates with the common output of the third and fourth gates, and for enabling either the fifth or sixth gate circuit but not both.

10. A device as claimed in claim 4, characterized in that:
- the irradiation means comprises four X-ray sources, one located at each corner of a square; and
- the extreme-value decoder comprises:
- first and second gate circuits having a common output, each gate circuit having an input coupled to an output of a storage section;
- a first comparator for comparing the outputs of the storage sections coupled to the first and second gate circuits and for enabling either the first or second gate circuit but not both;
- third and fourth gate circuits having a common output, each gate circuit having an input coupled to an output of a storage section;
- a second comparator for comparing the outputs of the storage sections coupled to the third and fourth gate circuits and for enabling either the third or fourth gate circuit but not both;
- fifth and sixth gate circuits having a common output which is the output of the extreme-value decoder, each gate circuit having an input coupled to a common output of the first and second or third and fourth gates; and
- a third comparator for comparing the common output of the first and second gates with the common output of the third and fourth gates, and for enabling either the fifth or sixth gate circuit but not both.

* * * * *